Figure 3:
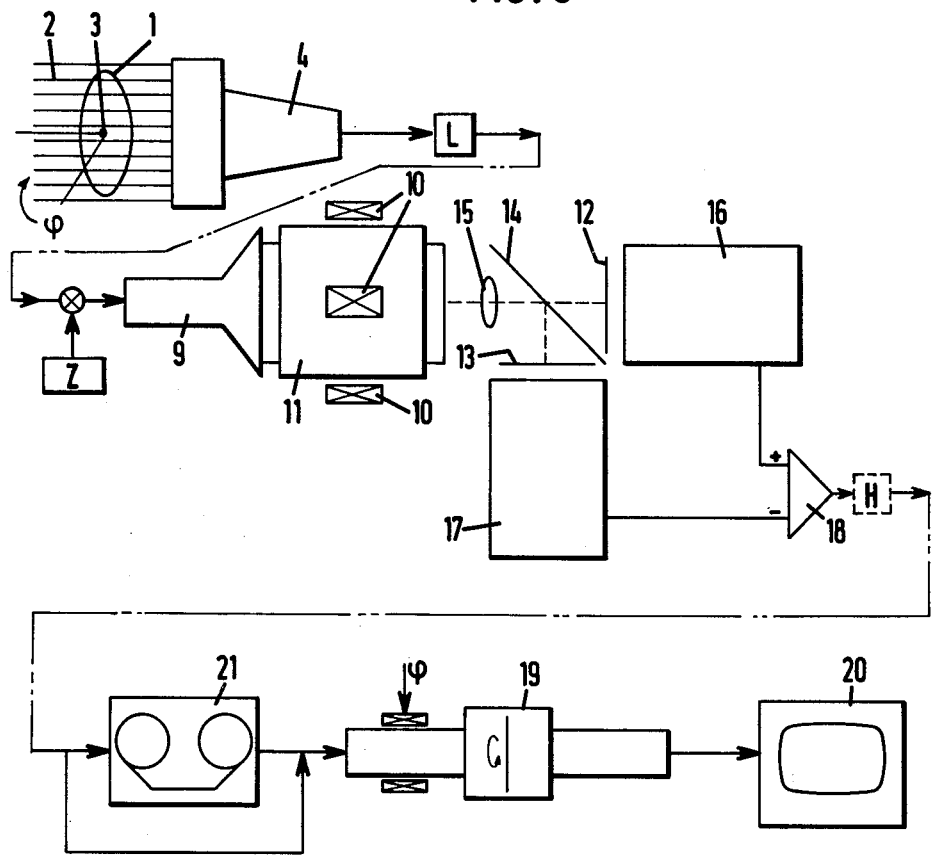

United States Patent [19]

Geluk

[11] 4,173,720
[45] Nov. 6, 1979

[54] METHOD AND APPARATUS FOR IMAGE CONSTRUCTION

[75] Inventor: Ronald J. Geluk, Nootdorp, Netherlands

[73] Assignee: N.V. Optische Industrie "De Oude Delft", Netherlands

[21] Appl. No.: 795,238

[22] Filed: May 9, 1977

[30] Foreign Application Priority Data

May 17, 1976 [NL] Netherlands ............... 7605254

[51] Int. Cl.² .......................... A61B 6/00; A61B 6/02
[52] U.S. Cl. .......................... 250/445 T; 250/416 TV; 358/111; 364/414
[58] Field of Search ............... 250/445 T, 416 TV; 364/414; 358/111

[56] References Cited

U.S. PATENT DOCUMENTS 4,023,036  5/1977  Barrett et al. ............... 250/445 T Primary Examiner—Alfred E. Smith
Assistant Examiner—T. N. Grigsby
Attorney, Agent, or Firm—O'Brien and Marks

[57] ABSTRACT

A tomogram is constructed from a plurality of profiles by means of back projection, the effect of the point spread function being eliminated by analog convolution with a suitable one- or two-dimensional function.

33 Claims, 4 Drawing Figures

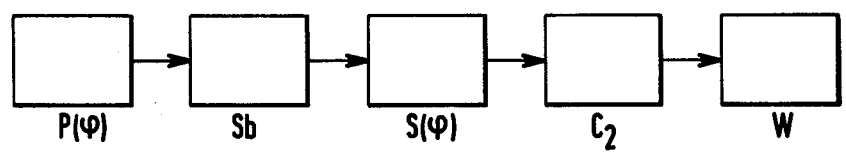
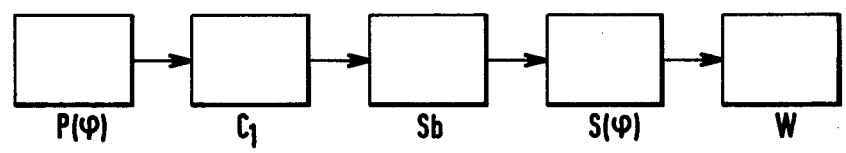
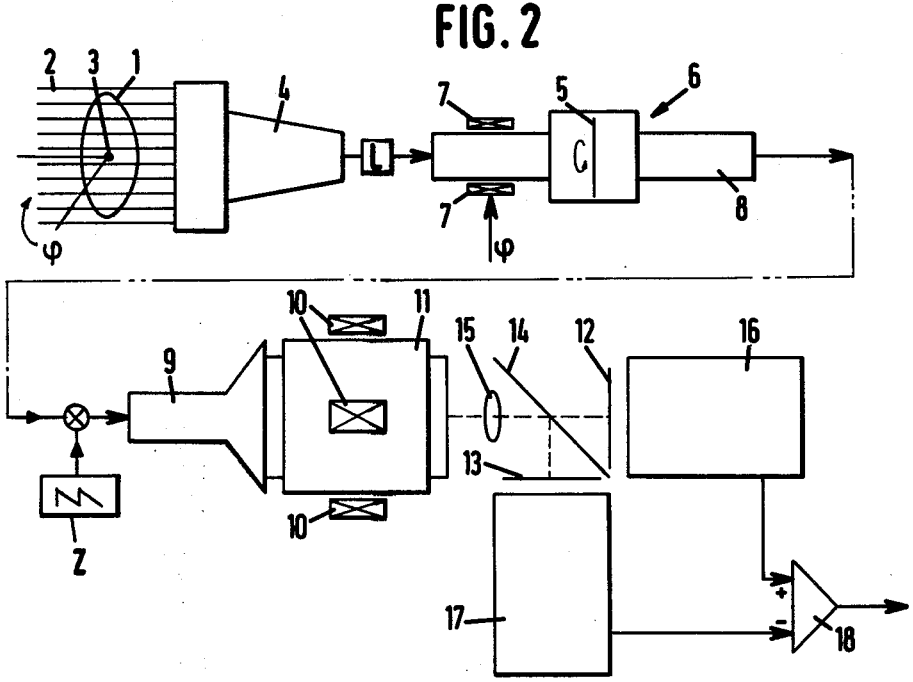

METHOD AND APPARATUS FOR IMAGE CONSTRUCTION

The present invention relates to a method and an apparatus for the construction of a tomogram from a plurality of profiles by means of back projection. A tomogram is an image of a cross-section of a body. A profile in this connection is a reproduction of the transmission variation or the absorption variation of the body measured along a line co-planar with the cross-section, as described in German Offenlegungsschrift No. 2017441.

It is known, starting from a plurality of profiles, each corresponding to a specific angle of rotation of the body about an axis perpendicular to the plane of the required cross-section, to construct a cross-sectional image by means of back projection. To this effect a so-called line image (Strichbild) is made of each profile in that the profile is extended for instance perpendicular to the direction of the transmission or absorption variation. In case the profiles are obtained by irradiation of a section of the body by means of X-rays, a profile consists of a series of points situated on a line of varying luminance, while a line image derived from such a profile comprises a series of juxtaposed lines, the luminance from line to line being a reproduction of that of the points of the profile, while the luminance of each line, over the entire length of the line, is constant. In order to construct a tomogram the lines of the line image should at least be as long as the largest size of the cross-section to be examined transversely to the profile. By superposition of all resulting line images, each line image having the same orientation relative to the other line images as did the corresponding profile relative to the other profiles, there is obtained an approximation of the desired tomogram.

A drawback going with the above method for forming a tomogram is that in the construction of the tomogram from the line images, an image point is built up from a fan of lines, while only a common intersection of the fan represents the required image point. This method, also called the summation method or the method of lineary superposition, leads to particularly blurred images.

This will be shown by the following:

each point of the profile has an associated line in each line image. Upon superposition of the line images, said lines intersect each other at the point in question, so that a point is produced also in the constructed image. Furthermore the intersecting lines emanating from the point constitute a star pattern. Upon superposition of a plurality of line images, there is produced a blur around each point. The intensity variation of said blur is represented by means of the point spread function. Said function is very extensive so that the image obtained after back projection is substantially blurred.

Hitherto mostly photographic techniques have been employed in image constructions with back projection, which were time-consuming, while the elimination of the disturbing effect of the point spread function required complicated and lenghty mathematical operations, such as convolution of the image obtained after back projection with a suitable function or convolution of each profile with such a function that, after the back projection, the required sharp tomogram is produced immediately. These drawbacks also apply in case computer techniques are employed.

It is the object of the present invention to remove the above drawbacks. To this effect, according to the invention, a method of constructing a tomogram from a plurality of profiles by means of back projection is characterized in that analog convolution with a suitable function is applied.

According to a further elaboration of the inventive idea, the analog convolution may be performed either with a two-dimensional function in order to convert a blurred image formed already by means of back projection into a sharp image, or by means of a one-dimensional function, whereby prior to the back projection each profile is first convolved with such a function that after back projection there is immediately obtained a sharp image.

Two embodiments according to the invention will now be described, by way of examples, with reference to the accompanying drawings wherein FIGS. 1A and 1B diagrammatically show a number of successive stages of the two methods according to the invention for forming a tomogram.

FIG. 2 diagrammatically shows an embodiment of an apparatus for forming a tomogram by means of two-dimensional convolution of the back projection.

FIG. 3 diagrammatically shows an embodiment of an apparatus for forming a tomogram by means of one-dimensional convolution of the profiles.

FIG. 1A shows a method comprising successive stages ($P(\phi)$, $S_b$, $S(\phi)$, $C_2$, and W. At $P(\phi)$ the profiles or projections associated with different angles of rotation of the body to be examined are formed; at $S_b$ line images are formed from the profiles; at $S(\phi)$ said line images are superimposed, each time taking into account the angle $\phi$ associated with the profile underlying the line image. The blurred image obtained by superposition of the line image, or a signal representing said blurred image, is convolved analogly at $C_2$ with a suitable two-dimensional function ($F(x,y)$). The function $F(x,y)$ can be determined from the following equation:

$$\int_{x=-\infty}^{+\infty} \int_{y=-\infty}^{+\infty} (PSF) \cdot F(x,y) \, dx \, dy = \delta(x,y)$$

wherein PSF indicates the (known) point spread function and $F(x,y)$ the two-dimensional convolution function and $\delta(x,y)$ the Dirac's function. After completion of the two-dimensional convolution the result is represented at W or further processed.

FIG. 1B deviates from FIG. 1A to such extent that immediately after forming the profiles at $P(\phi)$ the profiles themselves are convolved at C1 with a suitable one-dimensional function $F(x)$. Subsequently, the convolved profiles are converted at $S_b$ into line images which are superimposed at $S(\phi)$, whereafter the reproduction or further processing takes place at W.

It is observed that it is also possible to first form the line images, and subsequently to convolve each of said line images with a suitable function while thereafter performing the superposition. Such a method, however, does not basically deviate from the method rendered in FIG. 1A and will not be further described in the following.

FIG. 2 diagrammatically shows an apparatus for forming a tomogram, use being made of a rapid analog convolution of an image obtained by back projection. By 1 is indicated a body, for instance a patient, of which a tomogram is to be made. The body 1 is irradiated with for instance a beam of parallel X-rays 2 and it can rotate about a shaft 3 extending perpendicularly to the plane of drawing. The beam of X-rays has a slight thickness perpendicular to the plane of drawing, so that only a thin section of the body is irradiated. It is observed that, although the invention is described in the scope of tomograms to be obtained by means of X-rays, the invention is not restricted to the use of X-rays, nor to the use of parallel rays. In practice the X-rays mostly converge. In such case line images are formed of which the juxtaposed lines converge as well. However, this is not of relevance to the present invention.

By irridiating in the above described manner a thin section of the body 1, there can be obtained at the other side a striplike image the intensity of which varying in the direction of the strip, corresponding with the density of the body in situ. To each angle of rotation $\phi$ of the body there is associated such a striplike image, in general called "profile" or "projection".

The resulting profiles are processed to an electric signal, e.g. by means of an X-ray television circuit 4, as for instance described in Dutch patent application No. 75,03862.

The X-ray television circuit is preferably also used to form from the profiles the associated line images. To this effect the television scan lines extend transversely to the profiles, there being applied a holding circuitry which holds the respective luminance information each time during one line period. In such case electric T.V. signals are applied to the scan-convertor which represent the line images formed. It is also possible to form the line images only in the scan-converter, in which case electric signals are applied to said scan-converter which represents the profiles taken up. The recording electron beam in the scan-convertor is then so influenced by means of known per se electron-optical means that the transversely extending profiles, so the line images, are written on the target.

On the target of a scan-converter the line images associated with the profiles are now superimposed, whereby the proper angle $\phi$ is each time adjusted for instance by rotating the yoke, not shown, on which the deflection coils 7 are mounted.

The adjustment of the angle $\phi$ should be effected very accurately in order to avoid image errors, in particular blur of the eventual image. Since the output signals of the X-ray television circuit 4 representing the profiles represent the cumulative multiplication of transmission factors occurring in the body, along the X-ray trajectories while theoretically an addition should take place for reconstruction, said signals are first made logarithmic, as indicated by L.

The resulting blurred charge image is again scanned by a scan portion 8 of the scan convertor and reproduced on the screen of a cathode ray tube 9. Said screen should be a persisting screen, so that the writing electron ray of tube 9 can be turned off before the convolution operation takes place. The convolution operation may be performed suitably by means of a luminance amplifier 11 provided with deflection coils 10, and masks 12, 13 of which the one comprises the positive part of the convolution function F(x,y) and the other the negative part. The image in the luminance amplfier is deflected by means of a suitable control of the deflection coils such that it periodically moves over the anode of the luminance amplifier, and so that it is imaged on the masks 12, 13, via a beam splitter 14, possibly by means of a lens system 15. Behind each mask there is disposed a photomultiplier tube 16, 17. The output signals of the photomultiplier tubes are combined by means of a suitable amplifier 18 and then represent the required sharp, image-signal which can be subsequently reproduced in known manner on a monitor and/or may be further processed. The described method of convolution by means of a luminance amplifier, a beam splitter, masks and photomultiplier tubes is already described in Dutch patent application No. 76,00155, which, in so far as necessary, is deemed to be incorporated in the present.

It is essential that the writing beam of the cathode ray tube 9 is not involved in the convolution. Since the apertures representing the function F(x,y) contained in the masks, extends over the entire image plane, it cannot be ensured that the writing beam is present beyond the aperture at the moment of convolution. The writing beam, consequently, should be inoperative during the convolution. The persistence time of the screen of the cathode ray tube should be so long that during said persistence time the convolution may take place.

Nevertheless a luminance difference will occur between the part of the image that was the first to be written and the subsequently written portions.

In order to counteract this effect, the writing electron beam in the cathode ray tube 9 is so modulated that the luminance variation of the persistence image already occurring durng writing is compensated. To this effect the intensity of the writing beam can be reduced during writing for instance by means of a sawtooth generator L. The input signal of the cathode ray tube is therefor multiplied by a sawtooth signal adapted to the persistence time of the screen.

FIG. 3 shows an apparatus for performing the method shown in FIG. 1B. Parts of FIG. 3 that correspond to parts of FIG. 2 are provided with the same reference numerals. In the apparatus shown in FIG. 3 the resulting profiles, after logarithmation at L, are first convolved with a suitable one-dimensional function (F(x), after which, through back projection, the required tomogram is immediately formed. An advantage of this method is that the convolution can be performed already during the writing of the successive profile. The function F(x) is determined similarly as the function F(x,y) during the two-dimensional convolution.

The profiles are again formed in the above described manner and are applied from the X-ray television circuit 4, after logarithmation, in the form of electric signals to the cathode ray tube 9. The successive profiles are now written in superimposed relationship on the screen of the cathode ray tube 9. Said screen again has a specific persistence time. The convolution operation takes place again by means of a luminance amplifier 11 provided with deflection coils 10, a beam splitter 14, masks 12, 13 and photomultiplier tubes 16, 17. The masks, however, now contain a linear, in principle one-dimensional aperture. Since the one-dimensional aperture does not extend over the entire image field, it is possible, if desired, to simultaneously write a signal on the screen of the cathode ray tube 9, scanning same by means of the luminance amplifier 11, while yet the writing beam is not involved in the convolution. (see also Dutch application No. 76,00155).

The output signal of amplifier 18 now represents each time the profiles convolved with F(x). The output signal of amplifier 18 representing the convolved profiles is again reproduced as line image on the target of the scan converter 19. For this purpose may be used, as already observed, a dotted hold circuit H having a hold period of one line period. Another possibility is the application of electron-optical means coacting with the scan converter. Similarly, as already indicated with respect to FIG. 2, the desired image is constructed by means of back projection on the target of a scan convertor, which image can be visualized in known manner by means of a monitor 20.

Since the writing of the profiles on the screen of the cathode ray tube takes place substantially simultaneously with the convolution operation, the construction of a tomogram can be effected so rapidly that during one revolution of the body to be examined, tomograms of a number of superimposed sections can be formed. In such case each section may require one scan convertor, because for each construction of a tomogram, a two-dimensional medium is required. Either a corresponding number of monitors can then be employed or one monitor, which each time is connected to the required scan convertor. It is also possible to apply a memory 21, for instance a video recorder, in order to store the convolved profiles. It will then be possible to consult the memory at any required period of time for each tomogram to be presented and to convert the associated profiles by means of back projection on the target of a single scan convertor.

We claim:

1. A method of constructing at least one tomogram from a plurality of profiles by means of back projection, characterized in that analog convolution with a suitable function is applied and being further characterized in that line images derived from the profiles are reproduced, summed, by means of back projection on a cathode ray tube having a presisting screen; that the residual image is convolved analogly by means of a luminance amplifier provided with deflection coils with a function $F(x,y)$ established in at least one mask disposed behind said luminance amplifier.

2. A method according to claim 1, characterized in that the profiles are made logarithmic prior to the back projection.

3. A method according to claim 2, characterized in that the summation of the line images takes place in a scan convertor.

4. A method according to claim 3, characterized in that the line images are formed by means of electron-optical means coacting with the scan convertor.

5. A method according to claim 1, characterized in that the line images are made logarithmic prior to being summed.

6. A method according to claim 5, characterized in that the summation of the line images takes place in a scan convertor.

7. A method according to claim 1 characterized in that the intensity of the writing beam of the cathode ray tube is modulated such that the luminance variation occurring during the writing of the image on the screen of the cathode ray tube is compensated.

8. A method according to claim 7, characterized in that the input signal of the cathode ray tube is multiplied by a correction signal.

9. A method of constructing at least one tomogram from a plurality of profiles by means of back projection, characterized in that analog convolution with a suitable function is applied and being further characterized in that profiles are written on the persisting screen of a cathode ray tube; that the written profiles are convolved analogly by means of a luminance amplifier provided with deflection coils with a function $F(x)$ established in at least one mask disposed behind the luminance amplifier; and that the required tomogram is formed from the convolved profiles by means of back projection.

10. A method according to claim 9, characterized in that the profiles are made logarithmic before the writing on the screen of a cathode ray tube takes place.

11. A method according to claim 9, characterized in that electric signals are formed corresponding to line images associated with the profiles by means of a hold circuitry with a suitable hold period.

12. A method according to claim 9, characterized in that during one revolution of the body to be examined, the profiles of more than one section of the body are convolved.

13. A method according to claim 12, characterized in that a separate scan converter is applied for the back projection of the convolved profiles associated with each section.

14. A method according to claim 13, characterized in that the convolved profiles are temporarily written in a memory and that the tomogram associated with each section is each time formed by supplying to a scan convertor the written, convolved profiles from the memory associated with the respective section.

15. A method according to claim 12, characterized in that for the back projection of profiles associated with a plurality of sections, use is made of a memory means and a single scan convertor.

16. A method according to claim 9, characterized in that the intensity of the writing beam of the cathode ray tube is modulated such that the luminance variation occurring during the writing of a profile on the screen of the cathode ray tube is compensated.

17. A method according to claim 16, characterized in that the input signal of the cathode ray tube associated with a profile is multiplied by a correction signal.

18. An apparatus for constructing at least one tomogram from a plurality of profiles by means of back projection, characterized by an X-ray television circuit 4 for picking up the profiles; a scan convertor 6 connected to the output of said circuit having deflection coils 7; a cathode ray tube 9 connected to the output of the scan converter 6 having a persisting screen; an analogous convolution apparatus 10-18 for the analog convolution of the residual image of the cathode ray tube with a two-dimensional convolution function $F(x,y)$ established in one or more masks 12, 13.

19. An apparatus according to claim 18, characterized by a logarithmation device L connected between the X-ray television circuit (4) and the scan convertor (6).

20. An apparatus according to claim 18, characterized by electronoptical means coacting with the scan convertor for forming line images.

21. An apparatus according to claim 18 characterized by a ramp signal generator which is connected to the input of the cathode ray tube through a modulator.

22. An apparatus for constructing at least one tomogram from a plurality of profiles by means of back projection, characterized by an X-ray television circuit 4 for picking up the profiles; a scan convertor 6 connected to the output of said circuit; a cathode ray tube 9 connected to the output of said scan convertor an analog convolution apparatus 10-18 in succession to the cathode ray tube for the analog convolution of the profiles written on the screen of the cathode ray tube with a one-dimensional convolution function F(x) established in one or more masks 12, 13; a memory 21 and processing apparatus 19, 20 connected to the output of the convolution apparatus; and being further characterized by a logarithmation device connected between the X-ray television circuit (4) and the scan convertor (6).

23. An apparatus for constructing at least one tomogram from a plurality of profiles by means of back projection, characterized by an X-ray television circuit 4 for picking up the profiles; a cathode ray tube 9 connected to the output of said circuit; an analog convolution apparatus 10-18 in succession to the cathode ray tube for the analog convolution of the profiles written on the screen of the cathode ray tube with a one-dimensional convolution function F(x) established in one or more masks 12, 13; a memory and processing apparatus connected to the output of the convolution apparatus; and being further characterized in that the processing apparatus comprises a scan converter.

24. An apparatus according to claim 23, characterized by electronoptical means associated with the scan convertor for forming line images.

25. An apparatus according to claim 23, characterized by a hold circuitry in succession to the analog convolution apparatus for forming line images.

26. An apparatus according to claim 23, characterized in that the memory is a video recorder.

27. An apparatus according to claim 25, characterized by a ramp signal generator which is connected to the input of the cathode ray tube through a modulator.

28. An apparatus according to claim 22 characterized by a ramp signal generator which is connected to the input of the cathode ray tube through a modulator.

29. A method according to claim 2, characterized in that the intensity of the writing beam of the cathode ray tube is modulated such that the luminance variation occuring during the writing of the image on the screen of the cathode ray tube is compensated.

30. A method according to claim 3, characterized in that the intensity of the writing beam of the cathode ray tube is modulated such that the luminance variation occurring during the writing of the image on the screen of the cathode ray tube is compensated.

31. A method accoring to claim 4, characterized in that the intensity of the writing beam of the cathode ray tube is modulated such that the luminance variation occurring during the writing of the image on the screen of the cathode ray tube is compensated.

32. A method accoring to claim 5, characterized in that the intensity of the writing beam of the cathode ray tube is modulated such that the luminance variation occurring during the writing of the image on the screen of the cathode ray tube is compensated.

33. A method according to claim 6, characterized in that the intensity of the writing beam of the cathode ray tube is modulated such that the luminance variation occurring during the writing of the image on the screen of the cathode ray tube is compensated.

* * * * *